United States Patent

Wolf

[11] Patent Number: 5,929,241
[45] Date of Patent: Jul. 27, 1999

[54] PROCESS FOR THE PREPARATION OF AN ISOCYANATE-FREE URETDIONE OF ISOPHORONE DIISOCYANATE

[75] Inventor: Elmar Wolf, Recklinghausen, Germany

[73] Assignee: Huels Aktiengesellschaft, Marl, Germany

[21] Appl. No.: 09/004,301

[22] Filed: Jan. 8, 1998

[30] Foreign Application Priority Data

Jan. 20, 1997 [DE] Germany .................. 197 01 714

[51] Int. Cl.$^6$ .................. C07D 401/04; C07D 213/02
[52] U.S. Cl. .................. 546/193; 546/276.4; 546/304
[58] Field of Search .................. 544/222; 540/202; 546/193, 304, 276.4

[56] References Cited

FOREIGN PATENT DOCUMENTS

| | | |
|---|---|---|
| 0 045 995 | 2/1982 | European Pat. Off. . |
| 0 317 744 | 5/1989 | European Pat. Off. . |
| 0 735 027 | 10/1996 | European Pat. Off. . |
| 0 780 377 | 6/1997 | European Pat. Off. . |

*Primary Examiner*—Zinna Northington Davis
*Attorney, Agent, or Firm*—Oblon, Spivak, McClelland, Maier & Neustadt, P.C.

[57] ABSTRACT

A process for the preparation of an isocyanurate-free uretdione of isophorphone diisocyanate, comprising dimerizing an isophorone diisocyanate of the general formula:

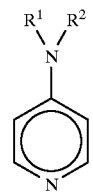

in an inert organic solvent or in the absence of a solvent, with the aid of a catalysts, at a temperature of 0 to 80° C.; isolating the uretdione formed from the reaction mixture after a conversion of 5–70%, without prior deactivation of the catalyst, by thin film distillation at 100–180° C. under 0.01–0.5 mbar; wherein the isophorone diisocyanate has a purity of $\geq 99.9\%$ by weight, and the concentration of the unknown first runnings component in a gas chromatogram of the isophorone diisocyanate employed for the dimerization is not greater than 0.05 area%; and wherein $R^1$ and $R^2$ are identical or different alkyl radicals having 1–8 C atoms, or with the N atom bonded to the ring, can form a common 5- or 6-membered ring which can contain a CH—CH$_3$ group, an N—CH$_3$ group or an O atom instead of a CH$_2$ group.

20 Claims, No Drawings

PROCESS FOR THE PREPARATION OF AN ISOCYANATE-FREE URETDIONE OF ISOPHORONE DIISOCYANATE

BACKGROUND OF THE INVENTION

1. Field of the Invention

The present invention relates to a process for the preparation of a uretdione of 3-isocyanatomethyl-3,5,5-trimethylcyclohexyl isocyanate (isophorone diisocyanate, IPDI).

2. Description of the Related Art

The dimer of isophorone diisocyanate (abbreviated as "IPDI-uretdione" below) is an important starting compound for the preparation of polyurethane powder (PUR) hardeners which are free from blocking agents, such as described in DE 30 30 588; 30 30 539; and 30 30 572, and which are gaining appreciably in importance as a result of the ever more stringent government regulations on environmental protection.

(Cyclo)aliphatic uretdiones, inter alia also IPDI-uretdione, were described for the first time in DE-OS 16 70 720, tertiary phosphines being employed as catalysts. However, these uretdiones comprise the corresponding isocyanurates as an impurity to a considerable extent. Dimerization of IPDI in accordance with the process described in DE-OS 16 70 720 also gives no uretdione but only a mixture of reaction products which comprises IPDI-uretdione to a maximum of 80% by weight. The remainder is trimeric isophorone diisocyanate which cannot be separated off.

DE-OS 19 34 763 relates exclusively to oligomerization of IPDI with tertiary phosphines. The reaction products obtained in accordance with the disclosure of DE-OS 19 34 763 comprise about 60 parts by weight of dimeric (can be cleaved under the action of heat) and trimeric or more highly oligomerized (can no longer be cleaved under the action of heat) IPDI. By suitable process variants (for example low conversion), the dimer proportion can be increased further to about 75 parts by weight. A further increase in the uretdione content is no longer possible, since the catalyst (tertiary phosphines) catalyzes not only the dimerization but also the trimerization of IPDI to give the corresponding isocyanurate.

An isocyanurate-free IPDI uretdione is described for the first time in DE-PS 30 30 513. The catalysts employed are phosphoric acid triamides, specifically trisdimethylaminophosphine. A disadvantage of this process is that hexamethylphosphorous acid triamide, which is known to be suspected of being carcinogenic according to Br. J. Cancer 38, 418–427 (1978), becomes concentrated in the reaction product during continuous preparation of IPDI-uretdione, in which the catalyst is circulated. This disadvantage of concentration of a substance suspected of being carcinogenic in the IPDI-uretdione was to be eliminated by use of the dimerization catalysts for IPDI described in DE-OS 37 39 549 (dialkylaminopyridines substituted in the 4-position). These 4-dialkylaminopyridines, specifically 4-dimethylaminopyridine (DMAP), have become accepted for the preparation of IPDI-uretdione on an industrial scale.

The IPDI quality employed to date for dimerization of IPDI is that such as is obtained by phosgenation of isophoronediamine (DE-PS 12 02 785):

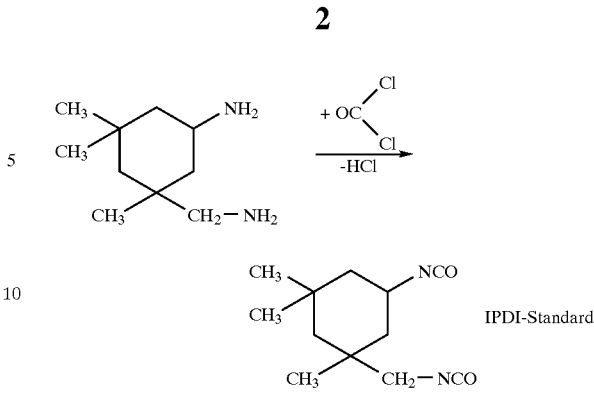

This standard IPDI comprises about 180 mg/kg of total chlorine, of which the hydrolyzable chlorine content is about 120 mg/kg.

DE-OSS 38 28 033 and 42 14 236 or 42 31 417 describe a process for the preparation of IPDI which dispenses with the use of highly toxic phosgene:

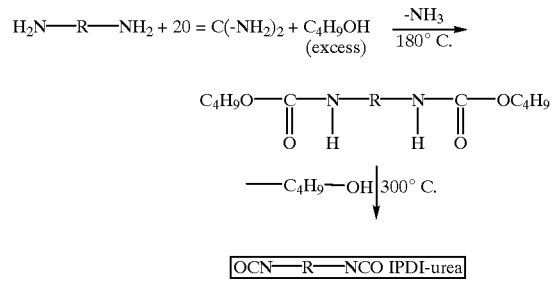

An IPDI which is chlorine-free and abbreviated as "IPDI-urea" below is obtained in this process. If the two IPDI qualities—IPDI-standard and IPDI-urea (99.6% of IPDI, as determined by gas chromatography (GC))—are compared in respect of the reaction with alcohols or of trimerization, hardly any differences are detected in these reactions. In contrast, if an attempt is made to dimerize IPDI-urea with 4-dimethylaminopyridine (DE-OS 37 39 549), highly colored reaction products, which in addition comprise small amounts of trimeric IPDI, are obtained. This phenomenon cannot be explained, since the reaction properties of IPDI should be independent of the process for its preparation. An IPDI which is unsuitable for the preparation of IPDI-uretdione would be severely limited in its possible uses.

The object of the present invention was therefore to prepare a non-discolored IPDI-uretdione from IPDI-urea.

SUMMARY OF THE INVENTION

Accordingly, one object of the present invention is to provide a non-discolored IPDI-uretdione from IPDI-urea.

The present invention relates to a process for the preparation of an isocyanurate-free uretdione of isophorone diisocyanate; the process of the present invention comprising dimerizing an isophorone diisocyanate having a purity of $\geq 99.9\%$ by weight which level of purity is denoted by an unknown first runnings component in the gas chromatogram of isophorone diisocyanate of not greater than 0.05 area percent, in the presence of an aminopyridine catalyst of the formula:

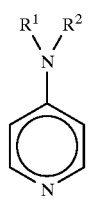

in which $R^1$ and $R^2$ are identical or different $C_1$–$C_8$ alkyl radicals; or with the N atom bonded to the ring, $R_1$ and $R_2$ can form a common 5- or 6-membered ring, which can contain a CH—$CH_3$ group, an N—$CH_3$ group or an O atom instead of a $CH_2$ group; and isolating the uretdione product from the reaction mixture upon a conversion of 5–70% of the starting isophorone diisocyanate without prior deactivation of the catalyst.

The dimerization is carried out in an inert organic solvent or free from solvent, with the aid of a catalyst at a temperature of 0–80° C., preferably at a temperature of 10 to 30° C.; the uretdione formed is then isolated from the reaction mixture after a conversion of 5–70% by weight, preferably at a conversion of 20–60% by weight, more preferably at a conversion of 40–50% by weight, without prior deactivation of the catalyst.

The isolation is carried out by thin film distillation at 100–180° C. under 0.1–0.5 mbar pressure; where the concentration of the unknown first runnings component in the gas chromatogram of the isophorone diisocyanate employed for the dimerization is not greater than 0.05 area %.

DESCRIPTION OF THE PREFERRED EMBODIMENTS

The IPDI which can be employed for the dimerization is described, for example, in EP 0568 782. While a content of unknown first runnings components of 0.3% (as determined by the area % of the GC) does not manifest itself adversely in the reaction with polyols and the trimerization, these unknown first runnings components must be no greater than 0.05% (as determined by the area of the GC) in the IPDI employed for dimerization if severe discolorations in the reaction product are to be avoided. Such an IPDI quality is as a rule obtained if the IPDI prepared in accordance with EP 0568 782 is fractionated to such an extend that the content of IPDI is ≧99.9%.

Suitable dimerization catalysts include, but are not limited to 4-dialkylaminopyridines, such as, for example, 4-dimethylaminopyridine, 4-diethylaminopyridine, 4-pyrrolidinopyridine, 4-piperidinopyridine and 4-(4-methylpiperidino)-pyridine. Preferred amount for the catalyst is from 0.2–4% by weight, a more preferred amount is 0.5–2% by weight. 4-dimethylaminopyridine (DMAP) and 4-pyrrolidinopyridine are particularly suitable.

The process according to the invention can in principle be carried out continuously and discontinuously.

The process according to the invention is preferably carried out by the first reacting IPDI-urea with the aid of a catalyst described, up to a conversion which still allows conveying of the reaction mixture in the liquid state at room temperature (an IPDI conversion of about 40–60% by weight), and then separating off the unreacted IPDI-urea with the catalyst from the reaction product by thin film distillation, in particular by molecular distillation. The IPDI-urea plus catalyst distilled off can be employed again for the reaction. The reaction time, the time in which 40–60% by weight of the IPDI-urea has reacted, depends (at a constant temperature) greatly on the concentration and on the nature of the catalyst employed. It is as a rule 40–90 hours. The reaction can be carried out in polar solvents, such as esters, ethers and ketones, or free from any solvent. It is preferably carried out free from a solvent. As already stated, the reaction mixture is worked up by thin film distillation at 100–180° C. under 0.01–0.5 mbar. The IPDI-uretdione thus prepared by the process according to the invention is also suitable for the preparation of solvent-free one- and two-component coatings and polyurethane powder coatings. Room temperature in the context of the present application denotes a temperature of 25–30° C.

The disclosure of German priority application 197 01 714.2 filed Jan. 20, 1997, is hereby incorporated by reference.

Having generally described this invention, a further understanding can be obtained by reference to certain specific examples which are provided herein for the purpose of illustration only and are not intended to be limiting, unless otherwise specified.

TABLE 1

IPDI qualities employed for the dimerization:

| | | Purity (area % (GC)) | | | | Chlorine content | | Color | |
| | | First | IPDI | After- | % | | mg/kg | | number | Density |
| IPDI | | Runnings | cis + trans | runnings | NCO | $n^{25}_D$ | Total | Hydrolyzable | (Hazen) | (20° C.) |
| 1. | IPDI-Standard | 0.24 | 99.6 | 0.17 | 37.8 | 1.4821 | 190 | 120 | <5 | 1.061 |
| 2. | IPDI-urea; (99.6%) | 0.23 | 99.6 | 0.15 | 37.8 | 1.4822 | <10 | <10 | 10 | 1.061 |
| 3. | IPDI-urea; (99.9%) | 0.03 | 99.6 | 0.06 | 37.7 | 1.4821 | <10 | <10 | 5 | 1.061 |

EXAMPLE 1

1% of 4-dimethylaminopyridine (DMAP) was added to IPDI qualities 1–3 described in Table 1, and the mixtures were left to stand at room temperature under a blanket of $N_2$ for 3 days. The course of the reaction was monitored by determination of the refractive index and the NCO content. After a reaction time of 3 days, the unreacted IPDI was separated off from the reaction product by thin film distillation at 120° C./0.1 mbar. The composition of the reaction products is shown in the following Table 2:

TABLE 2

| IPDI quality | IPDI-standard (Comparison) | | | IPDI-urea; (99.6%) (Comparison) | | | IPDI-urea; (99.9%) (Process according to the invention) | | |
|---|---|---|---|---|---|---|---|---|---|
| | | | | Dimerization of Various IPDI Qualities | | | | | |
| Reaction time | 1 day | 2 days | 3 days | 1 day | 2 days | 3 days | 1 day | 2 days | 3 days |
| % NCO | 33.7 | 31.1 | 29.2 | 33.8 | 31.0 | 29.2 | 33.7 | 31.1 | 29.2 |
| $n^{25}_D$ | 1.4877 | 1.4908 | 1.4930 | 1.4876 | 1.4908 | 1.4928 | 1.4878 | 1.4908 | 1.4930 |
| Color number (Hazen) | 210 | 290 | 360 | 560 | 650 | 800 | 200 | 280 | 350 |
| | (−IPDI 1 120° C./0.1 mbar) | | | (−IPDI) 1 120° C./0.1 mbar) | | | (−IPDI 1 120° C./0.1 mbar) | | |
| % NCO residue | | 17.50 | | | 17.06 | | | 17.40 | |
| % IPDI | | 0.64 | | | 0.68 | | | 0.54 | |
| % DMAP | | 0.02 | | | 0.03 | | | 0.02 | |
| Color number (Hazen) (70% strength in butyl acetate) | | 290 | | | not measurable 6 (Gardner) | | | 280 | |
| Isocyanurate | | | | | about 2% | | | | |
| GPC Analysis | | | | | | | | | |
| Mw | | 508 | | | 522 | | | 498 | |
| Mn | | 489 | | | 496 | | | 479 | |
| U | | 0.038 | | | 0.052 | | | 0.040 | |
| SFC Analysis Recoverable proportions by weight % | | 99.3 | | | 92.7 | | | 98.6 | |

GPC: Gel permeation chromatography
SFC: Superfluid chromatography
U = $Mw/M_n$ − 1

What is claimed as new and is desired to be secured by Letters Patent of the United States is:

1. A process for the preparation of an isocyanurate-free uretdione of isophorone diisocyanate, comprising:

dimerizing an isophorone diisocyanate having a purity of ≧99.9% by weight, which level of purity is denoted by an unknown first runnings component in the gas chromatogram of isophorone diisocyanate of not greater than 0.05 area percent, in the presence of an aminopyridine catalyst of the formula:

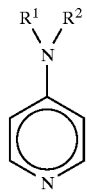

wherein $R^1$ and $R^2$ are identical or different $C_1$–$C_8$ radicals; or with the N atom bonded to the ring, $R^1$ and $R^2$ form a common 5- or 6-membered ring, which optionally contains a CH—$CH_3$ group, an N—$CH_3$ group or an O atom instead of a $CH_2$ group; and isolating the uretdione product from the reaction mixture upon a conversion of 5–70% of the starting isophorone diisocyanate without prior deactivation of the catalyst.

2. The process as claimed in claim 1, wherein said step of dimerizing is carried out in the presence of a catalyst and said step of isolating is carried out without prior deactivation of said catalyst.

3. The process as claimed in claim 1, wherein said step of dimerizing is carried out in an inert organic solvent.

4. The process as claimed in claim 1, wherein said step of dimerization is carried out at a temperature of 0 to 80° C. and said isolation step is carried out by thin film distillation at 100° C.–180° C. under 0.01 to 0.5 mbar pressure.

5. The process as claimed in claim 1, wherein said step of dimerizing is carried out at a temperature of 10–30° C.

6. The process as claimed in claim 1, wherein said step of isolating is carried out after a conversion of 20 to 60%.

7. The process as claimed in claim 6, wherein said step of isolating is carried out after a conversion of 40 to 50%.

8. The process as claimed in claim 2, wherein said catalyst is selected from the group consisting of 4-dimethylaminopyridine, 4-diethylaminopyridine, 4-pyrrolidinopyridine, 4-piperidinopyridine and 4-(4-methylpiperidino)-pyridine.

9. The process as claimed is claim 2, wherein said catalyst is selected from the group consisting of 4-dimethylaminopyridine and 4-pyrrolidinopyridine.

10. The process as claimed in claim 2, wherein said catalyst is employed in an amount of 0.2 to 4% by weight.

11. The process as claimed in claim 10, wherein said catalyst is employed in an amount of 0.5 to 2% by weight.

12. The process as claimed in claim 3, wherein said organic solvent is a polar solvent.

13. The process as claimed in claim 12, wherein said polar solvent is selected from the group consisting of an ester, an ether and a ketone.

14. The process as claimed in claim 1, wherein said step of dimerizing is carried out free of solvent.

15. An isocyanurate-free uretdione of isophorone diisocyanate obtained by the process of claim 1.

16. The isocyanurate-free uretdione of isophorone diisocyanate of claim 15, wherein said step of dimerizing, is carried out at a temperature of 10–30° C.

17. The isocyanurate-free uretdione of isophorone diisocyanate of claim 15, wherein said step of isolating is carried out after a conversion of 20 to 60%.

18. The isocyanurate-free uretdione of isophorone diisocyanate of claim 15, wherein said step of isolating is carried out after a conversion of 40 to 50%.

19. The isocyanurate-free uretdione of isophorone diamine of claim 15, wherein said catalyst is selected from the group consisting of 4-dimethylaminopyridine, 4-diethylaminopyridine, 4-pyrrolidinopyridine, 4-piperidinopyridine and 4-(4-methylpiperidino)-pyridine.

20. The isocyanurate-free uretdione of isophorone diisocyanate of claim 15, wherein said catalyst is selected from the group consisting of 4-dimethylaminopyridine and 4-pyrrolidinopyridine.

* * * * *